United States Patent
Nelson, Jr. et al.

(10) Patent No.: US 9,857,267 B1
(45) Date of Patent: Jan. 2, 2018

(54) METHODS AND APPARATUS FOR MEASURING SMALL LEAKS FROM CARBON DIOXIDE SEQUESTRATION FACILITIES

(71) Applicant: Aerodyne Research, Inc., Billerica, MA (US)

(72) Inventors: David D. Nelson, Jr., N. Chelmsford, MA (US); Scott C. Herndon, Littleton, MA (US)

(73) Assignee: Aerodyne Research, Inc., Billerica, MA (US)

( * ) Notice: Subject to any disclaimer, the term of this patent is extended or adjusted under 35 U.S.C. 154(b) by 0 days.

(21) Appl. No.: 15/350,925

(22) Filed: Nov. 14, 2016

(51) Int. Cl.
| | |
|---|---|
| *G01J 3/00* | (2006.01) |
| *G01M 3/38* | (2006.01) |
| *G01N 21/27* | (2006.01) |
| *G01N 33/00* | (2006.01) |
| *G01N 21/05* | (2006.01) |

(52) U.S. Cl.
CPC .............. *G01M 3/38* (2013.01); *G01N 21/05* (2013.01); *G01N 21/27* (2013.01); *G01N 33/004* (2013.01); *G01N 33/0036* (2013.01); *G01N 2201/06113* (2013.01); *G01N 2201/12* (2013.01)

(58) Field of Classification Search
CPC ......... G01M 3/38; G01N 21/05; G01N 21/27; G01N 21/31; G01N 21/552; G01N 33/0036; G01N 33/004
See application file for complete search history.

(56) References Cited

U.S. PATENT DOCUMENTS

| 6,040,574 A | 3/2000 | Jayne et al. |
| 7,301,639 B1 | 11/2007 | Kebabian et al. |

(Continued)

OTHER PUBLICATIONS

Gu "An Eddy Covariance Theory of Using $O_2$ to $CO_2$ Exchange Ratio to Constrain Measurements of Net Ecosystem Exchange of Any Gas Species" Agricultural and Forest Meteorology vol. 176, pp. 104-110, 2013.

(Continued)

*Primary Examiner* — Abdullahi Nur
(74) *Attorney, Agent, or Firm* — Cesari and McKenna, LLP; James A. Blanchette

(57) ABSTRACT

In one embodiment, a $CO_2$ leak detection instrument detects leaks from a site (e.g., a $CO_2$ sequestration facility) using rapid concentration measurements of $CO_2$, $O_2$ and optionally water concentration that are achieved, for example, using laser spectroscopy (e.g. direct absorption laser spectroscopy). Water vapor in the sample gas may not be removed, or only partially removed. The sample gas may be collected using a multiplexed inlet assembly from a plurality of locations. $CO_2$ and $O_2$ concentrations may be corrected based on the water concentration. A resulting dataset of the $CO_2$ and $O_2$ concentrations is analyzed over time intervals to detect any changes in $CO_2$ concentration that are not anti-correlated with $O_2$ concentration, and to identify a potential $CO_2$ leak in response thereto. The analysis may include determining eddy covariance flux measurements of subsurface potential carbon.

29 Claims, 2 Drawing Sheets

(56) References Cited

U.S. PATENT DOCUMENTS

| | | |
|---|---|---|
| 7,704,746 B1 | 4/2010 | White et al. |
| 8,359,167 B2 | 1/2013 | Keeling et al. |
| 9,250,175 B1 | 2/2016 | McManus |
| 9,261,457 B1 | 2/2016 | Nelson |
| 2010/0241363 A1* | 9/2010 | Keeling ............... G01N 33/004 702/24 |
| 2015/0000374 A1 | 1/2015 | Romanak et al. |

OTHER PUBLICATIONS

Gu et al "The Fundamental Equation of Eddy Covariance and its Application in Flux Measurements" Agricultural and Forest Meteorology vol. 152, pp. 135-148, 2012.

Keeling et al "The Atmospheric Signature of Carbon Capture and Storage" Philosophical Transactions of the Royal Society A vol. 369, pp. 2113-2132, 2011.

Lee et al "A Perspective on Thirty Years of the Webb, Pearman and Leuning Density Corrections" Boundary-Layer Meteorology vol. 139, pp. 37-59, 2011.

McManus et al "Recent Progress in Laser-Based Trace Gas Instruments: Performance and Noise Analysis" Applied Physics B vol. 119, pp. 203-218, 2015.

Pak et al "Early Atmospheric Detection of Carbon Dioxide from Carbon Capture and Storage Sites" Journal of the Air & Waste Management Association vol. 66, pp. 739-747, 2016.

Van Leeuwen et al "Detection of CO2 Leaks from Carbon Capture and Storage Sites with Combined Atmospheric CO2 and O2 Measurements" International Journal of Greenhouse Gas Control vol. 41, pp. 194-209, 2015.

Webb et al "Correction of Flux Measurements for Density Effects Due to Heat and Water Vapor Transfer" Quarterly Journal of the Royal Meteorological Society vol. 106, pp. 85-100, 1980.

Zahniser et al "Measurement of Trace Gas Fluxes Using Tunable Diode Laser Spectroscopy" Philosophical Transactions of the Royal Society of London A vol. 351, pp. 371-382, 1995.

* cited by examiner

METHODS AND APPARATUS FOR MEASURING SMALL LEAKS FROM CARBON DIOXIDE SEQUESTRATION FACILITIES

STATEMENT REGARDING FEDERALLY SUPPORTED RESEARCH

This invention was made with Government support under DE-SC0013132 awarded by the Department of Energy. The Government has certain rights in this invention.

BACKGROUND

Technical Field

The present disclosure relates generally to carbon dioxide ($CO_2$) leak detection and more specifically to methods and apparatus for measuring leaks from a site, such as a $CO_2$ sequestration facility.

Background Information

Since the beginning of the industrial revolution, the human race has been burning larger and larger quantities of fossil fuels and emitting greater and greater amounts of $CO_2$ into the atmosphere in the process. The atmospheric burden of $CO_2$ has increased dramatically and continues to rise. This causes more heat to be trapped at the Earth's surface, driving surface temperatures higher. Further, significant quantities of excess $CO_2$ are dissolving in the oceans, making them more acidic. In general, the release of $CO_2$ into the atmosphere is driving dangerous global climate change.

One proposed approach for mitigating the atmospheric burden of $CO_2$ is long term carbon capture and storage (CCS). In this approach, $CO_2$ is captured, concentrated, and then stored in a sequestration facility, rather than being emitted into the atmosphere. Typically, storage involves pumping the concentrated $CO_2$ into underground geologic formations, where it is retained. In order to provide benefits, the $CO_2$ needs to be retained for thousands of years. During such time, it is important for both human safety and to achieve the intended environmental benefits that any leakage from the facility be detected and addressed. Such leakage may be quite small (e.g., 0.01% per year) and potentially dispersed across a wide area of ground above the facility. Even small, dispersed leaks are troublesome, as they can significantly reduce the climate change benefits of CCS.

Unfortunately, detecting (and potentially quantifying) small, dispersed leaks of $CO_2$ is quite challenging. One reason why such leak detection is challenging is the naturally high variability of $CO_2$ at the Earth's surface. $CO_2$ is continuously produced and consumed by a wide variety of ambient processes, such as fossil fuel combustion, photosynthesis, plant and soil respiration, etc. These local influences can lead to significant variations in the "natural" concentration of $CO_2$ close to ground level (e.g., variances of several parts per million (ppm) over a short period of time). It is difficult to detect small, dispersed leaks of $CO_2$ from a sequestration facility in the presence of this interference caused by "natural" processes.

One approach that has been investigated for detecting leaks of $CO_2$ is to mix a chemical tracer with the $CO_2$ that has a low background concentration and low natural variability, for example, a perfluorocarbon or $CO_2$ isotope. However, this approach has a number of disadvantages, which may include (depending on the tracer chosen), expense of the tracer, adverse environmental effects of the tracer, and potential for the tracer to move differently through geologic formations than the sequestered $CO_2$.

Another more promising approach involves simultaneously measuring atmospheric oxygen ($O_2$) in conjunction with $CO_2$ to discriminate between leaks of $CO_2$ from a sequestration facility and interference caused by "natural" sources. Changes in $CO_2$ and $O_2$ concentrations resulting from natural processes are generally anti-correlated. For example, in combustion $O_2$ is consumed and $CO_2$ is released. Likewise, in photosynthesis, $CO_2$ is consumed and $O_2$ is released. In contrast, there is generally little or no anti-correlation with $O_2$ concentration when a change in $CO_2$ concentration is the result of a leak from a sequestration facility.

Unfortunately, it is difficult to simultaneously measure $O_2$ in conjunction with $CO_2$ as required by this approach, in part because detecting $O_2$ at an optimal speed and at an optimal accuracy is challenging. One known technique for measuring $O_2$ and $CO_2$ involves separate $O_2$ and $CO_2$ analyzers. In this technique, the $O_2$ analyzer may use two fuel cells that include a lead anode and a gold cathode, one cell operating as a sample cell and the other as a reference cell. The current that is generated by the chemical reaction in each cell is linearly proportional to the partial pressure of the $O_2$ concentration in the cell. The separate $CO_2$ analyzer may use a non-dispersive infrared (NDIR) photometer to determine $CO_2$ concentration. The NDIR may have a single path, which is alternatively used with sample gas and a reference gas.

However, this existing technique for measuring $O_2$ and $CO_2$ has a number of shortcomings which has hindered its widespread deployment. First, this existing technique has insufficient measurement time resolution to observe concentration fluctuations that occur on time scales of less than one second to several seconds (it is only capable of a measurement every 3 minutes). Second, it requires elaborate calibration procedures and comparisons to reference standards. These requirements add cost, labor and the potential for installation errors. Third, it requires very near complete removal of naturally-occurring water vapor from the examined sample (e.g., removal to <1 parts per million by volume (ppmv)). This typically requires multiple stages of water removal structures, and operations such as cryogenic trapping, significantly complicating instrument design and operation, and requiring periodic replenishment of consumables. Fourth, it is generally unsuited for sampling at multiple locations across a sequestration facility, in part, because the calibration and water removal requirements, together with the use of separate $O_2$ and $CO_2$ analyzers, leads to a complex and expensive inlet assembly.

Accordingly, there is a need for improved methods and apparatus for measuring leaks from a site (e.g., a $CO_2$ sequestration facility) that may address some or all of these shortcomings.

SUMMARY

Methods and apparatus are provided for measuring leaks from a site (e.g., a $CO_2$ sequestration facility) using rapid concentration measurements of $CO_2$, $O_2$ and, optionally, water. When measurements are taken on the time scale of atmospheric mixing, concentration fluctuations caused by individual plumes or eddies may be captured. By analyzing such rapidly-captured measurements over short time intervals, calibration may be avoided as the concentration difference determinations are completed before significant instrument drift may occur. The availability of rapid concentration measurements for water may permit water concentration to be compensated for, avoiding the need to remove substantially all water vapor. Still further, rapid measurements may enable the use of a multiplexed inlet assembly to collect samples from dispersed locations about the site.

In one embodiment, a $CO_2$ leak detection instrument employs laser spectroscopy (e.g., direct absorption laser spectroscopy) to provide rapid measurements (e.g., a measurement frequency >=1 Hertz (Hz)) and short analysis time intervals (e.g., <=3 minutes). The $CO_2$ leak detection instrument includes a sample cell configured to receive sample gas (e.g., as a continuous flow) via an inlet assembly. The inlet assembly may lack water removal structures, such that water vapor in the sample gas is not removed, or may include a water removal structure capable of only partial water removal (e.g., 90% water removal). The inlet assembly may include a single sample inlet, or a plurality of sample inlets distributed at different locations across the site and a gas multiplexer that produces a sequentially multiplexed flow therefrom.

The $CO_2$ leak detection instrument includes a laser source configured to apply a beam to the sample cell, and an optical detector configured to receive the beam after passing though the sample cell and to measure signal intensity thereof. A controller is coupled to the laser source and the optical detector, and configured to control these components to perform measurements at the measurement frequency to build a dataset. The measurements may be performed without extensive calibration. Each measurement may involve operations to continuously acquire spectra for the sample gas in the sample cell, to organize the spectra into periodic time bins and average the spectra therein, to analyze the averaged spectra for $CO_2$ concentration, $O_2$ concentration and water concentration, and to correct the $CO_2$ concentration and $O_2$ concentration based on the water concentration.

The controller periodically analyzes the dataset over time intervals to detect any changes in $CO_2$ concentration that are not anti-correlated with $O_2$ concentration, and to identify a potential $CO_2$ leak in response thereto. The analysis may include determining eddy covariance flux measurements of sub-surface potential carbon (SPC) using wind speed data, for example, acquired from a separate anemometer.

It should be understood that a variety of additional features and alternative embodiments may be implemented other than those discussed in this Summary. This Summary is intended simply as a brief introduction to the reader for the further description which follows, and does not indicate or imply that the examples mentioned herein cover all aspects of the disclosure, or are necessary or essential aspects of the disclosure.

BRIEF DESCRIPTION OF THE DRAWINGS

The description below refers to the accompanying drawings of example embodiments, of which.

DETAILED DESCRIPTION OF AN ILLUSTRATIVE EMBODIMENT

Figure 1:
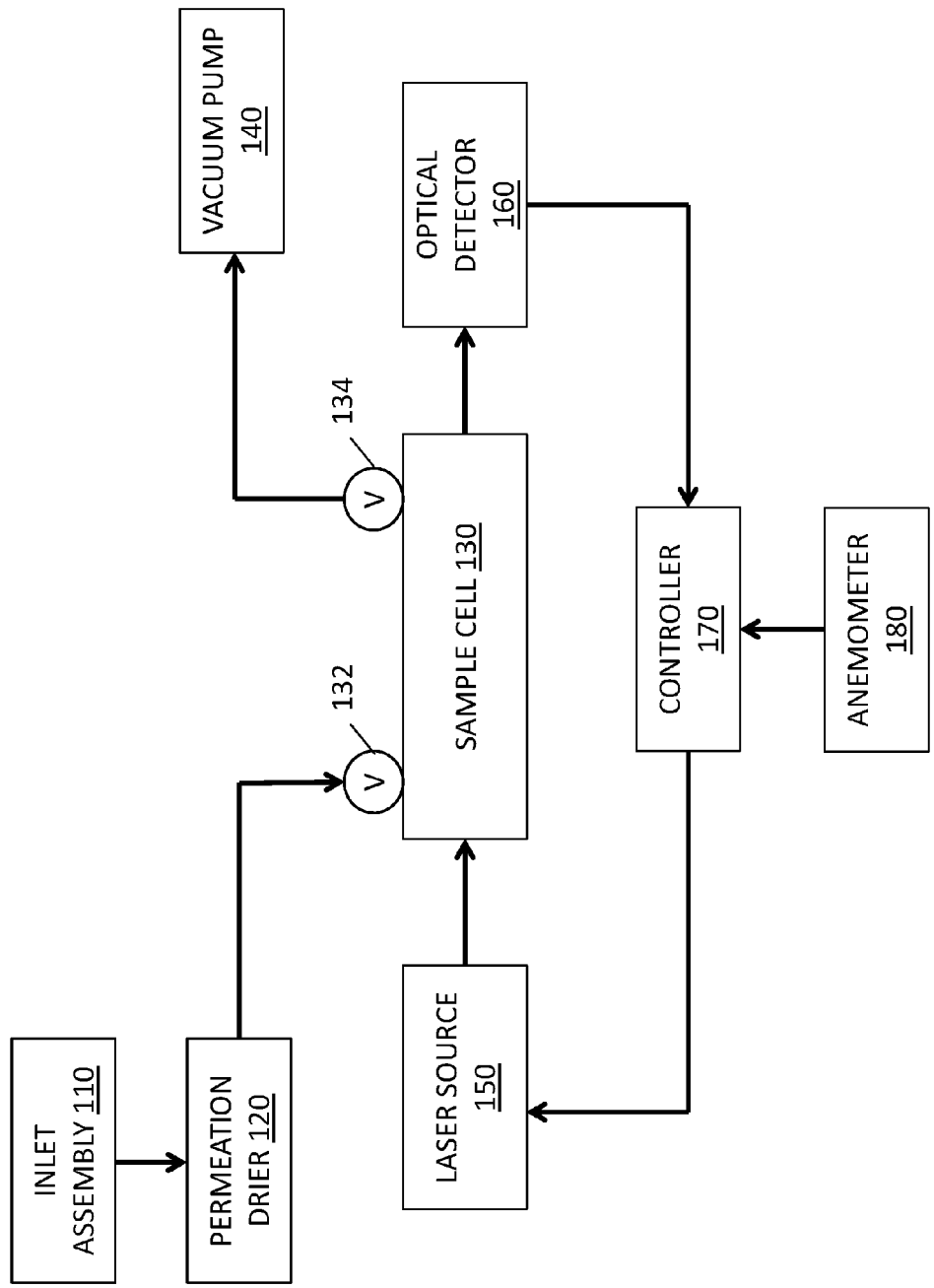
FIG. 1 is a block diagram of an example $CO_2$ leak detection instrument employing laser spectroscopy (e.g., direct absorption laser spectroscopy) that may be utilized to detect leaks from a site, such as a $CO_2$ sequestration facility.

FIG. 1 is a block diagram of an example $CO_2$ leak detection instrument employing laser spectroscopy (e.g., direct absorption laser spectroscopy) that may be utilized to detect leaks from a site, such as a $CO_2$ sequestration facility. An inlet assembly 110 collects gas (e.g., air) from the site. The inlet assembly may include a single sample inlet that capture sample gas from a single location, for example, at one substantially ground level location. Alternatively, in other embodiments, the inlet assembly may be a multiplexed inlet assembly that includes a plurality of sample inlets distributed (e.g., substantially at ground level) at different locations across the site (e.g., in a grid or radial pattern), and a gas multiplexer that includes fast-operating valves that are actuated to sequentially connect channels from each inlet to a common output to produce a sequentially multiplexed flow of sample gas from the different locations. The use of a multiplexed inlet assembly may be possible due to the instrument's high measurement frequency and ability to operate at low gas flow rates (e.g., <=3 standard liter per minute (SLPM)) on small samples (e.g., <=100 milliliters (ml) samples), as explained in more detail below.

The inlet assembly 110 may be coupled directly to a sample cell 130 of a laser spectrometer (e.g., a direct absorption laser spectrometer). In such an embodiment, naturally-occurring water vapor in the sample gas (e.g., air) is not removed prior to delivery of the sample gas to the sample cell. Alternatively, in other embodiments, a permeation drier 120 is capable of only partially removing water vapor from the sample gas is provided, such that no more than 90% of water vapor in the sample gas is removed prior to delivery of the sample gas to the sample cell (e.g., leaving potentially thousands of ppmv of water vapor in the sample gas). As explained in more detail below, water concentration may be measured along with $CO_2$ concentration and $O_2$ concentration, and the water concentration used to correct $CO_2$ concentration and $O_2$ concentration to account for varying dilution and spectroscopic effects caused thereby.

The sample cell 130 receives a continuous flow of sample gas through an inlet valve 132 which is expelled via an outlet valve 134 coupled to a vacuum pump 140. In one embodiment, the sample cell is a multi-pass cell (MPC) having a volume of 100 ml fed at a gas flow rate of approximately 3 SLPM.

A laser source 150 of the spectrometer (e.g., one or more tunable monolithic solid-state lasers, such as a quantum cascade laser (QCL), interband cascade laser (ICL) or tunable diode laser (TDL)) directs a beam (e.g., a frequency-swept beam) along an optical path of the sample cell 150 through the sample gas disposed therein. Under the direction of a programmable controller 170 (e.g., a computer executing software), the laser source 160 may sweep the frequency of the beam across the absorption lines of $CO_2$, $O_2$ and water. An optical detector 160 of the direct absorption spectrometer is configured to receive the beam after passing though the sample cell 130 and measure signal intensity. The programmable controller 170 is configured to use such arrangement to continuously acquire spectra. As explained in more detail below, the continuously acquired spectra are utilized by the controller 170 to produce a dataset of water-concentration-corrected measurements of $CO_2$ concentration and $O_2$ concentration. The controller periodically analyzes this dataset over time intervals to detect any changes in $CO_2$ concentration that are not anti-correlated with $O_2$ concentration and to identify a potential $CO_2$ leak in response thereto.

In some embodiments, where the analysis performed by the controller 170 includes determining eddy covariance flux measurements, an anemometer 180 may be coupled to the controller 170 and rapidly acquire and provide wind speed measurements thereto.

Figure 2:
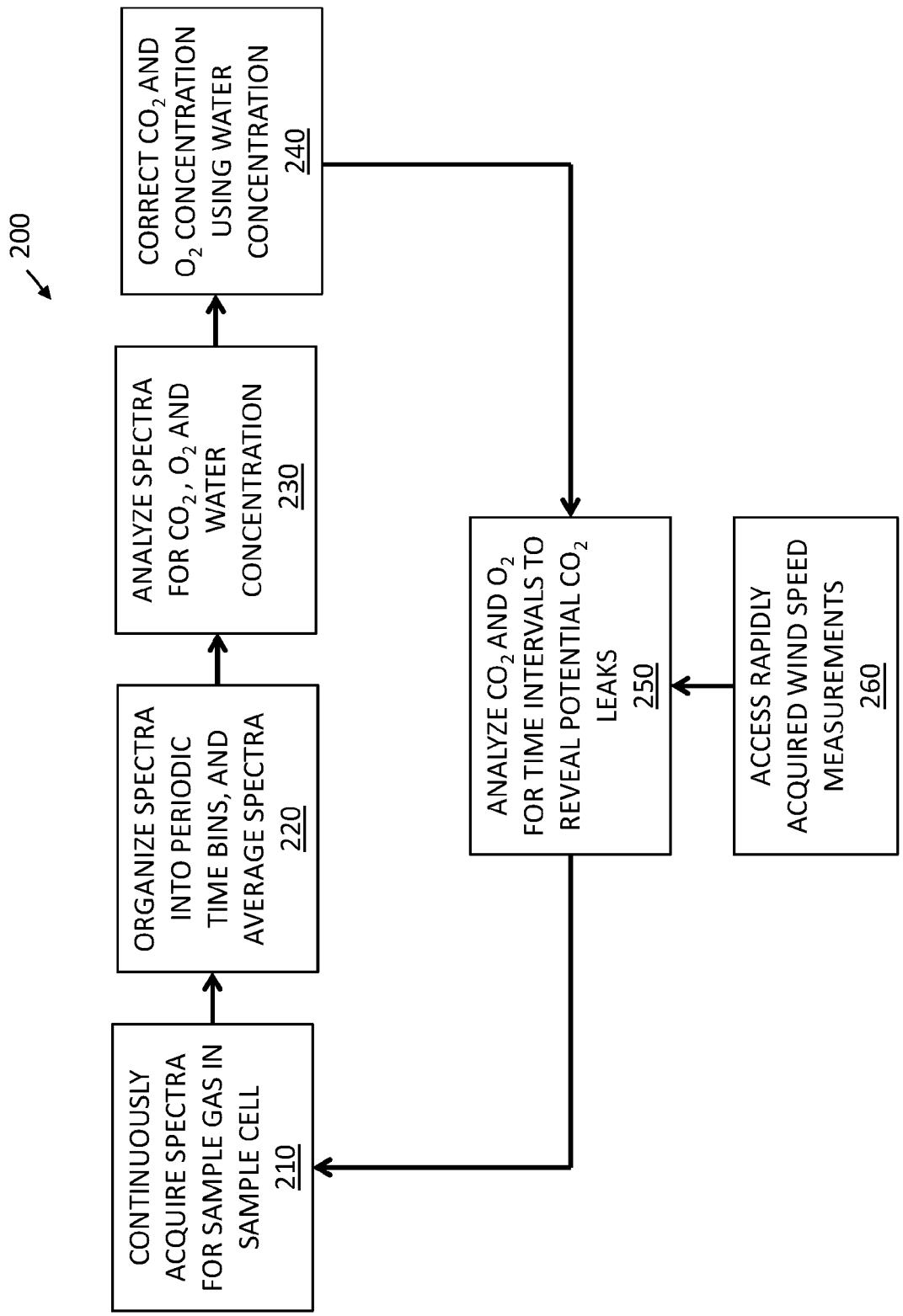
FIG. 2 is a flow diagram of a sequence of steps that may be executed by a controller to utilize the rapid measurements available from laser spectroscopy (e.g., direct absorption laser spectroscopy) to detect $CO_2$ leaks from a site, such as a $CO_2$ sequestration facility.

FIG. 2 is a flow diagram of a sequence of steps 200 that may be executed by the controller 170 to utilize the rapid measurements available from laser spectroscopy (e.g., direct absorption laser spectroscopy) to detect $CO_2$ leaks from a site, such as a $CO_2$ sequestration facility. The steps assume that that sample gas (e.g., air) has been subject to no, or only partial, water removal and is continuously flowing into the sample cell 130. However, the general operations of the steps 200 may be adapted to other configurations. Step 210-240 may be executed repeatedly at a rapid measurement frequency (e.g., $>=1$ Hz, for example 10 Hz) to produce a dataset of measurements. At step 210, spectra are continuously acquired for the sample gas in the sample cell 130 using the laser source 150 and optical detector 160. At step 220, the spectra are organized into periodic time bins (e.g., as small as 0.1 seconds (s)) and the spectra therein are averaged. At step 230, the averaged spectra are analyzed for $CO_2$ concentration, $O_2$ concentration and water concentration. The analysis is based on the Beer-Lamber law, where light transmitted through a sample gas as a function of frequency for an isolated line, $[l(v)]$, maybe expressed as:

$$l(v)=l_o(v)\exp[-(LN_o(P,T)MS(v,P,T))],$$

where $l_o(v)$ is the light output of the laser source 150 as a function of laser frequency, L is the absorption path length of the sample cell 130, $N_o$ is the molecular density number $(cm^{-3})$ as a function of pressure (P) and temperature (T), M is the concentration of the compound of interest, and $S(v, P, T)$ is the absorption line length as a function of frequency, pressure and temperature.

At step 240, the measured $CO_2$ concentration and $O_2$ concentration are corrected based on the water concentration to produce a combined measurement with is added to the dataset. The correction may compensate for both dilution and spectroscopic effects. For example, the presence of water vapor dilutes $CO_2$ concentration and $O_2$ concentration, lowering the concentrations compared to what would exist had water vapor been fully removed. A dilution correction may involve calculating the concentration of $O_2$ in the sample gas had water vapor been fully removed ($C_{O_2,dry}$) as:

$$C_{O_2,dry}=C_{O_2,wet}/(1-C_W),$$

where $C_{O_2,wet}$ is the $O_2$ concentration actually measured in the presence of water vapor and $C_W$ is the measured concentration of water.

Further, the presence of significant water vapor has spectroscopic effects because the spectral pressure broadening coefficients for water generally differ from those of a sample gas (e.g., air) with water vapor fully removed. A spectral correction may involve calculating a corrected pressure broadening coefficient. The spectra may be analyzed initially to determine the concentration of water, and then again using the concentration of water to specify a corrected pressure broadening coefficient for $CO_2$ and $O_2$. The corrected pressure broadening coefficient may be specified as:

$$PB_C=(1-C_W)*PB_{Gas}+C_W*PB_W,$$

where $PB_{Gas}$ is the pressure broadening coefficient that applies in a dry sample gas (e.g., dry air) and $PB_W$ is the pressure broadening coefficient that applies in pure water vapor.

At step 250, the dataset produced by the repeated execution of steps 210-240 is periodically analyzed by the controller 170, which examines short time intervals (e.g., $<=3$ minutes) to detect any changes in $CO_2$ concentration that are not anti-correlated with $O_2$ concentration, which is indicative of a potential $CO_2$ leak. The analysis may involve a number of different analysis techniques.

In one embodiment, the analysis may combine the dataset with rapidly acquired wind speed measurements, accessed at step 260, to measure eddy covariance flux, which may be used to detect, and to quantify, $CO_2$ leaks. $CO_2$ flux measurements via eddy covariance are insufficient since surface fluxes of $CO_2$ generally will exceed those from the subsurface resulting from leaks. To address this, instead of measuring fluxes of $CO_2$, the analysis measures the flux of SPC, where SPC is defined as:

$$SPC=[CO_2]+\alpha*[O_2],$$

where $\alpha$ is an average correlation coefficient of local processes that exchange $O_2$ for $CO_2$. The average correlation coefficient ($\alpha$) typically is about 0.9, but may vary with location, season, time of day and other conditions. Surface flux of SPC under normal conditions will average to zero. When a $CO_2$ leak occurs from underground storage, a SPC flux equals the flux of the leaked $CO_2$. While such analysis may be enabled by high speed and high precision detection of $O_2$ and $CO_2$, it is tolerant of slow instrument response drift because it is based on the correlation between concentration measurements and vertical wind speed, rather than absolute measures.

Alternatively, the analysis may involve time interval comparison, where scatter around a fitted slope for the time interval is compared in their mean and standard deviation with a scatter pattern that is considered "normal", and a potential $CO_2$ leak is identified based on a deviation. For example, a typical linear relationship may be determined for concentration of $O_2$ verses $CO_2$ using curve fitting. A $CO_2$ increase without coupled decrease in $O_2$ indicative of a leak is characterized by a deviation from the typical linear relationship resulting in larger scatter, and generally producing a larger standard deviation. Accordingly, a confidence (a) that a time interval contains a leak may be represented as:

$$\alpha = \frac{\mu_{interval} + \sigma_{interval}}{\sigma_{typical}},$$

where $\mu_{interval}$ is the mean for the time interval compared to the typical relationship, $\sigma_{interval}$ is the standard deviation for the time interval compared to the typical relationship, and $\sigma_{typical}$ is the standard deviation of the typical relationship. When $\alpha$ exceeds a predetermined threshold, the time interval may be identified to include a potential $CO_2$ leak.

Based on the results of the analysis in step 250, an indication of a potential $CO_2$ may be output by the controller 170 in a variety of ways, for example, displayed in a user interface on a screen, recorded in a log, used to trigger an alarm, etc.

In summary, the above description details methods and apparatus for measuring leaks from a site (e.g., a $CO_2$ sequestration facility) using fast measurements of $CO_2$, $O_2$ and, optionally, water concentration and short analysis time intervals. It should be understood that various adaptations and modifications may be made to what is described above, to suit various requirements of the particular detection site and other constraints. For example, while it is described above that direct absorption laser spectrometer may be used to perform the measurements of $CO_2$, $O_2$ and water concentration, it should be understood that other types of gas concentration measurement systems may be employed, including other types of laser spectrometers, spectrometers that do not utilize lasers, and differential fuel cells, among others, to determine one or more of these concentrations. A $CO_2$ leak detection instrument using an alternate approach to perform measurements may be able to achieve at least some of the advantages described above.

Further, it should be understood that many of the steps of the methods described above may be implemented automatically under the direction of software executing on one or more programmable controllers (e.g., computers) such as controller 170 or special purpose hardware (e.g., application specific integrated circuits (ASICs)), or may be implemented manually with an operator actuating controls of the apparatus. The implementation of the steps of the methods may be adapted to suit requirements of the particular detection site.

Above all, it should be understood that the above descriptions are meant to be taken only by way of example.

What is claimed is:

1. A carbon dioxide ($CO_2$) leak detection instrument, comprising
    a sample cell configured to receive sample gas via an inlet assembly from a site where $CO_2$ leaks are to be detected;
    a laser source configured to apply a beam to the sample cell;
    an optical detector configured to receive the beam after passing though the sample cell and to measure signal intensity thereof; and
    a controller coupled to the laser source and the optical detector and configured to perform measurements at a measurement frequency using the laser source and the optical detector to produce a dataset, each measurement to include:
        acquiring spectra for the sample gas in the sample cell, and
        analyzing the spectra for at least $CO_2$ concentration and atmospheric oxygen ($O_2$) concentration to produce combined measurements of $CO_2$ concentration and $O_2$ concentration that are added to the dataset,
    wherein the controller is further configured to analyze the dataset to detect any changes in $CO_2$ concentration that are not anti-correlated with $O_2$ concentration, and to identify a potential $CO_2$ leak in response thereto.

2. The $CO_2$ leak detection instrument of claim 1, wherein the controller uses the laser source and the optical detector operate to perform direct absorption spectroscopy to produce the data set.

3. The $CO_2$ leak detection instrument of claim 1, wherein the measurement frequency is greater than or equal to 1 Hertz (Hz).

4. The $CO_2$ leak detection instrument of claim 1, wherein the analysis of the dataset is performed periodically for the measurements in a time interval, wherein the time interval is less than or equal to 3 minutes.

5. The $CO_2$ leak detection instrument of claim 1, wherein the controller is configured to perform the measurements without calibration.

6. The $CO_2$ leak detection instrument of claim 1, wherein the inlet assembly lacks water removal structures, such that water vapor in the sample gas is not removed prior to delivery of the sample gas to the sample cell.

7. The $CO_2$ leak detection instrument of claim 1, wherein the inlet assembly includes a permeation drier configured to only partially remove water vapor from the sample gas, such that no more than 90% of water vapor in the sample gas is removed prior to delivery of the sample gas to the sample cell.

8. The $CO_2$ leak detection instrument of claim 1, wherein the analyzing the spectra further comprises analyzing the spectra for concentration of water, and each measurement further includes correcting $CO_2$ concentration and $O_2$ concentration based on the water concentration.

9. The $CO_2$ leak detection instrument of claim 1, wherein the sample gas is received as a continuous flow of sample gas, and the acquiring spectra comprises continuously acquiring spectra for the sample gas in the sample cell, organizing the spectra into periodic time bins and averaging the spectra therein, and the analyzing the spectra comprises analyzing the averaged spectra.

10. The $CO_2$ leak detection instrument of claim 1, wherein the controller is configured to access wind speed data, and wherein the analysis on the dataset comprises determining eddy covariance flux.

11. The $CO_2$ leak detection instrument of claim 10, wherein the determining eddy covariance flux measure flux of sub-surface potential carbon (SPC), where SPC is defined as:

$$SPC=[CO_2]+\alpha*[O_2],$$

where $\alpha$ is an average correlation coefficient of local processes that exchange $O_2$ for $CO_2$.

12. The $CO_2$ leak detection instrument of claim 10, wherein the inlet assembly is a multiplexed inlet assembly that includes a plurality of sample inlets distributed at different locations across the site and a gas multiplexer, the multiplexed inlet assembly configured to supply gas from the different locations sequentially as the sample gas.

13. A carbon dioxide ($CO_2$) leak detection instrument, comprising
    a sample cell configured to receive sample gas via an inlet assembly from a site where $CO_2$ leaks are to be detected;
    a gas concentration measurement system coupled to the sample cell; and
    a controller coupled to the gas concentration measurement system and configured to perform measurements at a measurement frequency using the gas concentration measurement system to produce a dataset, each measurement to include:
        determining $CO_2$ concentration, atmospheric oxygen ($O_2$) concentration and water concentration,
        correcting the $CO_2$ concentration and the $O_2$ concentration based on the water concentration, and
        adding the corrected $CO_2$ concentration and $O_2$ concentration to the dataset,
    wherein the controller is further configured to analyze the dataset to detect any changes in $CO_2$ concentration that are not anti-correlated with $O_2$ concentration, and to identify a potential $CO_2$ leak in response thereto.

14. The $CO_2$ leak detection instrument of claim 13, wherein the gas concentration measurement system comprises:
    a laser source configured to apply a beam to the sample cell; and
    an optical detector configured to receive the beam after passing though the sample cell and to measure signal intensity thereof.

15. The $CO_2$ leak detection instrument of claim 13, wherein the measurement frequency is greater than or equal to 1 Hertz (Hz).

16. The $CO_2$ leak detection instrument of claim 13, wherein the inlet assembly lacks water removal structures, such that water vapor in the sample gas is not removed prior to delivery of the sample gas to the sample cell.

17. The $CO_2$ leak detection instrument of claim 13, wherein the inlet assembly includes a permeation drier configured to only partially remove water vapor from the sample gas, such that no more than 90% of water vapor in the sample gas is removed prior to delivery of the sample gas to the sample cell.

18. A carbon dioxide ($CO_2$) leak detection instrument, comprising
a sample cell configured to receive sample gas via an inlet assembly from a site where $CO_2$ leaks are to be detected;
an anemometer located at the site;
a gas concentration measurement system coupled to the sample cell; and
a controller coupled to the measurement system and the anemometer and configured to perform measurements at a measurement frequency that include $CO_2$ concentration, $O_2$ concentration and wind speed, and to analyze the measurements to determine eddy covariance flux of sub-surface potential carbon (SPC) at the site, wherein presence of SPC indicates a potential $CO_2$ leak.

19. The carbon dioxide ($CO_2$) leak detection instrument of claim 18, wherein the gas concentration measurement system comprises:
a laser source configured to apply a beam to the sample cell; and
an optical detector configured to receive the beam after passing though the sample cell and to measure signal intensity thereof.

20. The $CO_2$ leak detection instrument of claim 18, wherein the measurement frequency is greater than or equal to 1 Hertz (Hz).

21. The $CO_2$ leak detection instrument of claim 18, wherein SPC is defined as:

$$SPC=[CO_2]+\alpha*[O_2],$$

where $\alpha$ is an average correlation coefficient of local processes that exchange $O_2$ for $CO_2$.

22. A method for carbon dioxide ($CO_2$) leak detection, comprising:
receiving a sample gas from a site where $CO_2$ leaks are to be detected;
performing measurements on the sample gas at a measurement frequency using a laser spectrometer, each measurement to include:
acquiring spectra for the sample gas, and
analyzing the spectra for at least $CO_2$ concentration and $O_2$ concentration to produce combined measurements of $CO_2$ concentration and $O_2$ concentration that are added to a dataset; and
analyzing the dataset, by a controller, to detect any changes in $CO_2$ concentration that are not anti-correlated with $O_2$ concentration and to identify a potential $CO_2$ leak in response thereto.

23. The method for $CO_2$ leak detection of claim 22, wherein the measurement frequency is greater than or equal to 1 Hertz (Hz).

24. The method for $CO_2$ leak detection of claim 22, wherein the measurements are performed without calibration.

25. The method for $CO_2$ leak detection of claim 22, wherein no more than 90% of water vapor in the sample gas is removed prior to performing measurements on the sample gas.

26. The method for $CO_2$ leak detection of claim 22, wherein the analyzing the spectra further comprises analyzing the spectra for concentration of water, and the performing measurements further includes correcting $CO_2$ concentration and $O_2$ concentration based on the water concentration.

27. The method for $CO_2$ leak detection of claim 22, wherein the sample gas is received as a continuous flow, and in the acquiring spectra comprises continuously acquiring spectra for the sample gas, organizing the spectra into periodic time bins and averaging the spectra therein, and the analyzing the spectra comprises analyzing the averaged spectra.

28. The method for $CO_2$ leak detection of claim 22, wherein the analyzing the dataset comprises determining eddy covariance flux of sub-surface potential carbon (SPC).

29. The method for $CO_2$ leak detection of claim 22, wherein the receiving receives a sequentially multiplexed flow of gas from a plurality of sample inlets distributed at different locations across the site.

* * * * *